United States Patent [19]

Martin

[11] Patent Number: 4,479,491

[45] Date of Patent: Oct. 30, 1984

[54] INTERVERTEBRAL STABILIZATION IMPLANT

[76] Inventor: Felix M. Martin, 1124 Broadway, Quincy, Ill. 62301

[21] Appl. No.: 401,845

[22] Filed: Jul. 26, 1982

[51] Int. Cl.$^3$ .......................... A61F 5/04; A61B 17/18
[52] U.S. Cl. ..................................... 128/92 B; 128/69; 128/92 D; 3/1.91
[58] Field of Search .............. 3/1.91; 128/92 R, 92 B, 128/92 D, 92 E, 69

[56] References Cited

U.S. PATENT DOCUMENTS

| | | | |
|---|---|---|---|
| 4,047,524 | 9/1977 | Hall | 128/92 D |
| 4,170,990 | 10/1979 | Baumgart et al. | 128/92 D X |
| 4,401,112 | 8/1983 | Rezaian | 128/92 B |

FOREIGN PATENT DOCUMENTS

| | | | |
|---|---|---|---|
| 2649042 | 9/1978 | Fed. Rep. of Germany | 128/69 |
| 2254304 | 7/1975 | France | 128/92 D |

*Primary Examiner*—Ronald L. Frinks

*Attorney, Agent, or Firm*—Eduardo M. Carreras

[57] ABSTRACT

An intervertebral stabilization implant is described including an elongated central portion and a pair of reverse wings disposed at an angle of between 75° and 80° with respect to the elongated central portion of the implant. The method of utilizing the implant is also disclosed including exposing the pre-vertebral space as would be done in a Cloward's procedure. The vertebral disks below the luxating vertebra is widely resected, avoiding if at all possible the use of the intervertebral spreader. The A-P diameter of the vertebral bodies are measured and the intervertebral stabilizing implant of proper length is elected taking into account a small correction of the luxation of up to 2 millimeters maximum, which would upset the compression effect of the retaining wings over soft tissue and bone. The implant is inserted sideways, utlizing no force. After the posterior wing is barely in the canal it is rotated 90° so that the posterior wing rests behind the lower vertebra and the superior or anterior wing is in front of the reduced vertebra.

5 Claims, 9 Drawing Figures

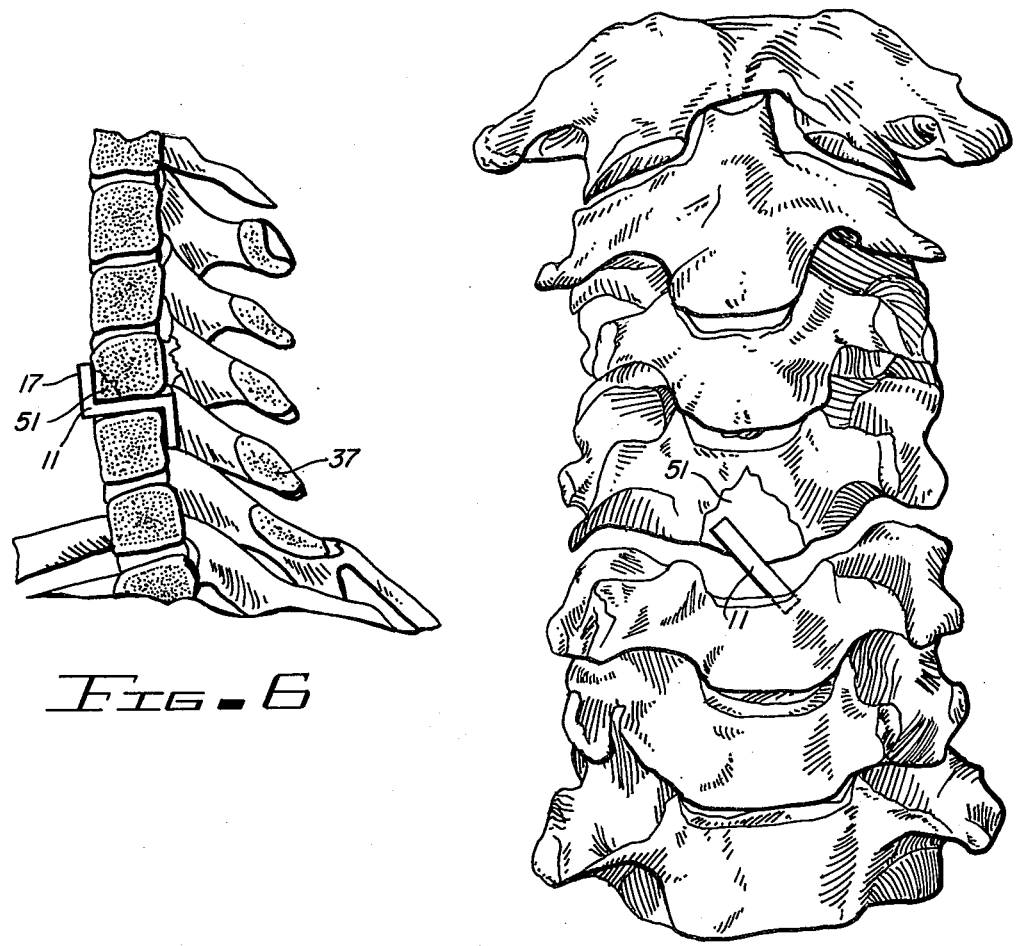
FIG-6
FIG-7
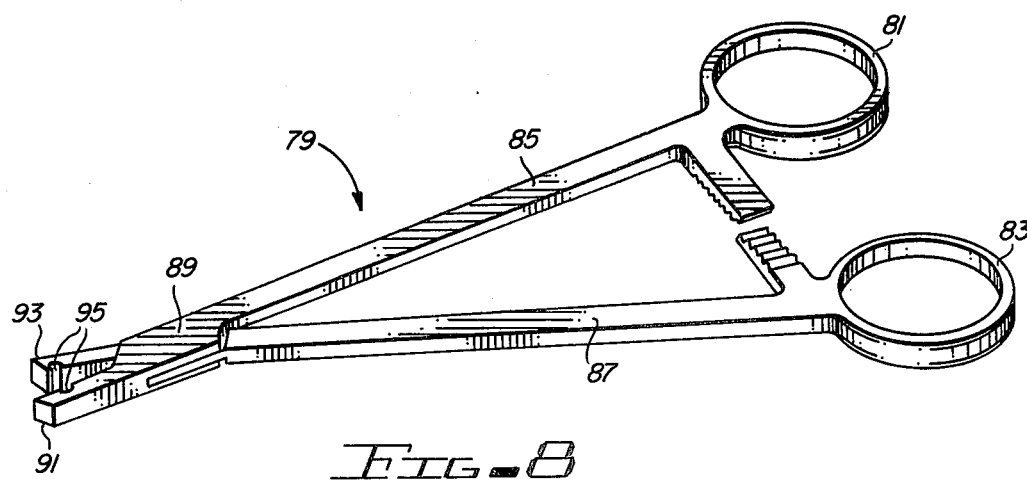
FIG-8

INTERVERTEBRAL STABILIZATION IMPLANT

BACKGROUND OF THE INVENTION

The present invention is directed to the managing of cervical spine injuries in general, more particularly to a new intervertebral stabilization implant for the managing of a cervical spine injury. The vertebral column consists of 33 vertebrae superimposed upon one another in a series which provides a flexible supporting column for the trunk and head. The vertebrae are separated by fibrocartilaginous intervertebral disks and are united by articular capsules and by ligaments. Of the fundamental 33 vertebrae, five are fused into the sacrum, and four combine in forming of the coccyx in the adult. The remaining 24 vertebrae are classified as seven cervical, twelve thoracic, and five lumbar.

The cervical vertebrae are the smallest of the series and are readily distinguishable by the presence of a large oval foramen in each transverse process. The body is small and somewhat broader from side to side than from front to back. The superior surface of the body is concave transversely with projecting lips on either side. The inferior surface is concave anteroposteriorly; its anterior lip projects downward to overlap the superior surface of the vertebrae below. The inferior surface is convex transversely to fit the transverse cavity of the superior surface of the next adjacent vertebrae. The pedicles project lateralward as well as backwards and spring from the body midway between its superior and inferior surfaces, so that the superior vertebral notch is steep as the inferior. Laminae are thinner above than below and enclose a larger, triangular vertebral foramen for the accommodation of the upper and larger portion of the spinal cord. The spinous process is short and bifid. The articular processes from prominent lateral projection from the junction of pedicles and laminae and three flat, oval facets. The superior facet are directed upwards, backwards and lightly medialward; the inferior facets face oppositely. Each transverse process is said to be perforated by the transverse foramen for the passage of the vertebral artery and vein and the vertebral nerve plexus. Actually, the "costotransverse" foramen is located between the transverse process posteriorally and a costal process anteriorally.

Various devices have been developed for the management of cervical spine injuries. One such device is a halo which consists of a stainless steel tiara affixed in four opposite positions to the skull by pins that penetrate the skin in external table. Treatment process includes maintaining the patent in traction for six weeks, then utilizing a "Minerva Jacket" for an additional six weeks or more. Most patients are stabilized with the device after twelve weeks. During the three month interval while intrinsic stability to the fractured spine is regained, the halo, either suspended on a plastic jacket or attached to a pelvic hoop permits early, safe mobilization under strong skeletal fixation. One of the disadvantages with halo braces is that they are likely to leave patients susceptible to neck pain developing late after cervical spine injury. It has been reported that about a third of the patients in halo braces sooner or later encounters instability or develops neck pain. (Convention Reporter, report on the Sixth Annual Scientific Meeting of the American Spinal Injury Association, Volume 10, No. 17, August, 1980).

Another device for stabilizing cervical injuries is an acrylic prothesis of the fifth cervical vertebra in multiple myeloma, as was reported in The Journal of Neurosurgery, Volume 35, p. 112, July 1971. In the procedure described in the above article, the collapsed fifth vertebral body is removed with rongeurs and curettes, exposing the anterior surface of the dura, the nerve roots, and portions of the vertebral arteries. The annulus and disks are removed from the interior surface of the fourth cervical vertebra and from the superior surface of the sixth cervical vertebra. A thick layer of Gel Foam moistened with saline was placed anterior to the dura. A piece of thin Tantalum shaped into a half cylinder was placed over the Gel Foam. A tantalum screw was then inserted into the interior surface of the body of the fourth cervical vertebra and into the superior surface of the body of the sixth cervical vertebra protruding into the fifth cervical interspace for a distance of 1 cm. With the use of a cervical traction apparatus the normal fifth cervical vertebra interspace was established. Methyl methacrylate powder and isomer were then mixed and shaped around the protruding screws in the form of a normal cervical vertebra. The disadvantage with the above described method is that it usually involved three cervical vertebrae and requires the removal of the fractured vertebra.

A metal prosthesis for the cervical vertebrae was disclosed in the Journal of Neurosurgery, Volume 42, May 1975, p. 562. The prosthesis described is a quadrilateral cylindrical member with a window in the front. The sizes of the prosthesis correspond to that of a cervical vertebra. The technique requires the removal of the affected vertebra and insertion of the prosthesis through an anterior approach, as in Cloward's anterior body fusion. Collapsed vertebral body is removed with rongeurs and curettes exposing the anterior surface of the dura. Annulus and disks were also removed from the upper and lower surfaces of the affected vertebra. Again, the procedure described in that reference requires the removal of the fractured vertebra and the involvement of two additional vertebrae. For other lesions of a destructive nature, like malignancies, the stabilization of the cervical spine has required the use of a combination of methacrylate and metal screws in normal bone above and below the destructive area in the vertebral body. Alternately, a cylinder-like device made of Tantalum is used to serve as a mold for the methacrylate that is used to replace the absent vertebral bodies. This latter approach has had limited success.

Other method of treating the fractures of the cervical spine include posterior stabilization surgical procedures which require the involvement of four vertebrae as a general rule and require the permanent immobilization of three of the intervertebral spaces. Long range effects in the rest of the cervical spine tend to increase with time. Usually, a second incision is required in order to obtain a bone graft. Another procedure is an anterior cervical fusion. This procedure requires a bone graft, usually from the ilium. The stability of the fracture site with good reduction after surgery would require at least five to six weeks. In the meantime, traction, collar, bed rest or other techniques must come into play in order to prevent destabilization of the reduced spine.

BRIEF SUMMARY OF THE INVENTION

An intervertebral stabilization implant is disclosed characterized by an elongated main member having a length substantially equal to the width of the body of the cervical vertebra to be immobilized, and having a superior retaining wing disposed at an angle of from 75° to 80° to the main member and an oppositely disposed posterior wing disposed at an angle of from 75° to 80° from the main member. The implant is placed with the superior (or anterior) wing adjacent to the anterior portion of the body of the involved vertebra, and the posterior wing adjacent to the posterior portion of the body of an adjacent vertebra. The implant thus serves to secure the fractured or luxated vertebra to an adjacent vertebra.

BRIEF DESCRIPTION OF THE DRAWINGS

Further details are explained below with the help of the examples illustrated in the attached drawings in which:

FIG. 6 is a cross sectional side view of the cervical vertebrae with the implant in place;

FIG. 7 is a front view of the cervical vertebrae showing the rotation of the implant after it has been inserted into the intervertebral space; and FIG. 8 is an isometric view of an instrument used for the insertion of the implant.

DETAILED DESCRIPTION OF THE INVENTION

Figure 1A:
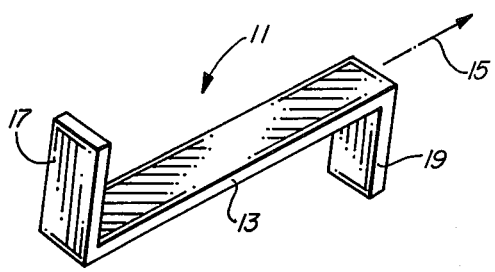
FIG. 1A is a perspective view of the implant according to the present invention.
Figure 1B:
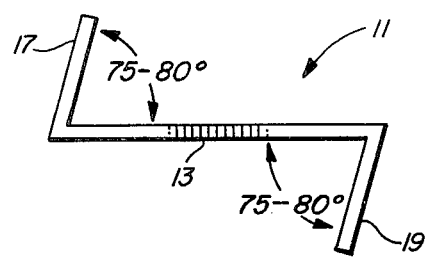
FIG. 1-B is a side view of the implant according to the present invention.

Illustrated in FIG. 1 is the intervertebral stabilization implant 11 according to the present invention. The implant 11 includes an elongated main portion 13 defining a longitudinal axis 15 on the implant 11. The implant also includes a superior (or anterior) wing portion 17 disposed at one end of the elongated main portion 13. The angle measured counter clockwise on the longitudinal axis 15 to the superior wing portion 17 should be between approximately 75° to 80°. The implant 11 also includes a posterior wing portion 19 disposed at the other end of the elongated main portion 13. The posterior wing portion 19 should be disposed so that the angle between the elongated main portion 13 and the posterior wing portion 19 is approximately 75° to 80°. The implant 11 should be made of an integral bar of surgical metal such as surgical steel and should be approximately 1 mm in thickness and approximately 3.5 to b 4 mm in width. The length of the elongated main portion 13 varies with the size of the portions of the vertebrae as will be explained below, but usually will fall between approximately 10 to 24 mm. In the preferred embodiment the posterior wing portion 19 is approximately 5 mm in length, while the superior wing portion 17 may be 5 to 7 mm in length, depending upon the type of fracture being treated.

Figure 2:
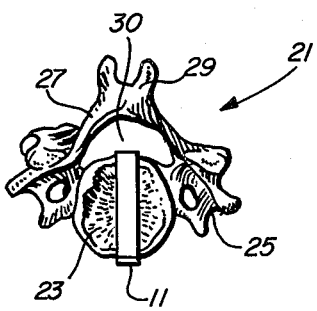
FIG. 2 is a top view of a cervical vertebra with the implant disposed thereon.

Illustrated in FIG. 2 is a top view of a typical cervical vertebra 21. As explained in the background of the invention, the cervical vertebra 21 includes a body portion 23, a pedicle 25, laminae 27, and the spinous process 29 and the vertebral foramen 30. Also illustrated in FIG. 2 is the intervertebral stabilization implant 11 as it would be disposed after insertion.

Figure 3:
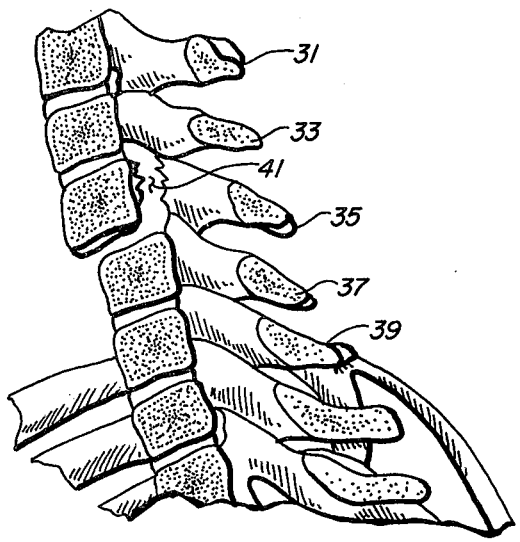
FIG. 3 is a cross sectional side view of the cervical vertebrae with a fracture of the lamina of the fourth cervical vertebra.
Figure 4:
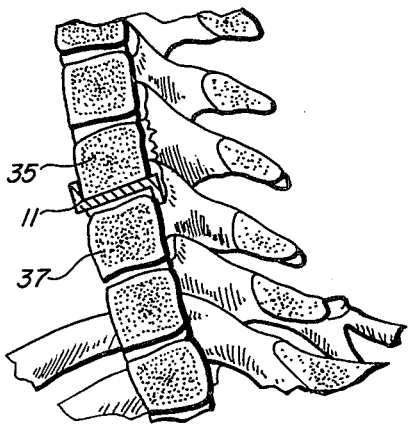
FIG. 4 is a cross sectional side view of the cervical vertebrae showing the implant and its side effect.

The function of the implant 11 is illustrated with reference to FIG. 3 and FIG. 4. FIG. 3 shows a cross sectional side view of the cervical vertebrae, including the second cervical vertebra 31, the third cervical vertebra 33, the fourth cervical vertebra 35, the fifth cervical vertebra 37 and the sixth cervical vertebra 39.

Figure 5:
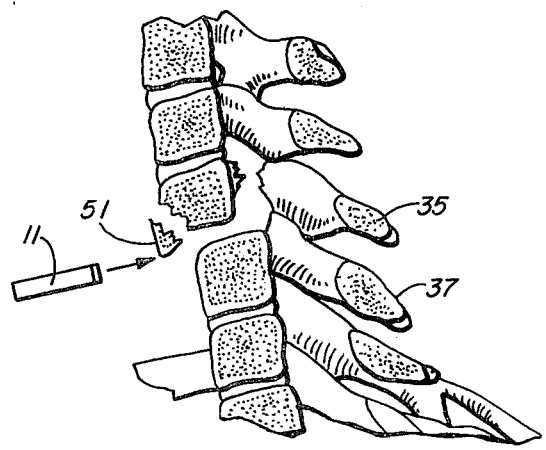
FIG. 5 is a cross sectional side view of the cervical vertebra with a tear drop fracture.

Illustrated in FIG. 3 is a fracture and luxation 41 of the fourth cervical vertebra 35. The luxation is illustrated by the relative dislocation of the fourth cervical vertebra 35 from the fifth cervical vertebra 37. It should be stressed that luxation can occur as a result of a fracture or as a result of degenerative disease. The implant 11 is used to treat the luxation. A fracture 41 is stabilized by an operation comprising the steps of exposing the pre-vertebral space as would be done in a Cloward's procedure. The intervertebral disk below the luxating vertebra is widely resected, avoiding if at all possible the use of the intervertebral spreader. Measurement of the lower vertebral body in antero-posterior projection is then carried out. The distance between the anterior portion of the body of the affected vertebra and the posterior portion of the body of an adjacent vertebra (e.g. the fifth cervical vertebra 37) is then measured and an intervertebral stabilizing implant 11 of proper length is selected taking into account a small over correction of the luxation up to 2 mm maximum which would upset the compression effect of the retaining wings 17 and 19 over soft tissue and bone. The implant 11 is inserted sideways as shown in FIG. 5. In case of luxation due to degenerative process, a moderate amount of force may be required. After the posterior wing 19 is barely in the spinal canal 30, the implant is rotated 90° so the posterior wing 19 rests behind the lower vertebra, in the illustration of FIG. 4 the fifth cervical vertebra 37, and the anterior wing rests in front of the affected vertebra, in the case of FIG. 4 the fourth cervical vertebra. After insertion, the head of the patient that has been in hyperextension in order to reduce the luxation is brought up close to the neutral position, with partial reduction of the intervertebral space. Routine closure is then performed, leaving 2, ¼" rubber drain in place. A "Philadelphia collar" is applied before the patient wakes up. Illustrated in FIGS. 5–8 is the equipment used and the procedure followed in the case of a tear drop fracture of a cervical vertebra. Illustrated in FIGS. 5, 6 and 7 is a tear drop fracture 51 on the body portion of the fourth cervical vertebra, with associated luxation. As shown in FIG. 6 an implant 11 can be used to stabilize the tear drop fracture 51. In this case, however, the implant 11 has a longer anterior wing 17 than the implant previously described. The same procedure as above, is performed and as illustrated in FIG. 7 the implant is inserted sideways and rotated 90° to secure the affected area by means of the implant to an adjacent cervical vertebra. The cartilage in between the vertebra is widely resected to enable the positioning of the implant.

It has been found that after the operation utilizing the disclosed implant the patient can move freely in bed from side to side. Surgeon can allow semi-Fowler's position if he deems it pertinent after the first day. Routinely, the patient is able to stand on the third day and may be discharged in seven to ten days. The technique has little morbidity, providing fast stabilization of the luxating vertebra. This implant can be used in the cervical spine below the second cervical vertebra 31. The technique was used satisfactorily in a patient with luxation of the third and fourth cervical vertebra due to severe degenerative process with progressive paraparesis.

Illustrated in FIG. 8 is an instrument 79 which is used to place the implant into the appropriate position. The instrument 79 includes a pair of finger handles 81 and 83 integrally formed on a pair of elongated instrument sections 85 and 87. The instrument sections 85 and 87 are pivotally connected at pivot 89. Instrument section 85 is provided with a tip 91 and instrument section 87 is provided with a tip 93. Each tip 91 and 93 have a substantially rectangular cross section, and tip 91 protrudes approximately 1.5 mm in comparison with tip 93. The width of each tip 91 and 93 should be approximately 4 mm. Each tip 91 and 93 are provided with a small groove 95 of approximately 1 mm in depth. The groove 95 can be formed by drilling in a hole 2 mm in diameter with its center at the contact point between instrument sections 85 and 87 and at a slight inward distance from the end of tip 93. The groove 95 allows the surgeon to grasp and position the stabilization implant 11.

It will thus be seen that the objects set forth above, among those made apparent from the preceding description, are efficiently attained, and, since certain changes may be made in the above article without departing from the scope of the invention it is intended that all matter contained in the above description, or shown in the accompanying drawings shall be interpreted as illustrative and not in a limiting sense. Additionally, since certain changes may be made in carrying out the disclosed method without departing from the scope of the invention, it is intended that all matter illustrative of the method containing the description of the drawings, shall be interpreted as illustrative and not in a limiting sense.

I claim:

1. An implant for the stabilization of a fractured and luxated cervical vertebra comprising:
    a retaining member having a longitudinal portion extending at least the distance between the posterior of the body of a cervical vertebra adjacent to the fractured and luxated vertebra and the anterior of the body of the fractured or luxated cervical vertebra; a posterior wing downwardly disposed at an angle at one end of the longitudinal portion and adapted to be engaged by the posterior edge of the body of the adjacent cervical vertebra and a superior wing upwardly disposed at an angle at the other end of the longitudinal portion of said superior wing adapted to engage the superior edge the body portion of the fractured or luxated vertebra whereby the natural action of the muscles associated with the neck maintain the fractured or luxated vertebra in compression against the superior wing and the posterior wing engages the body portion of the adjacent vertebra to prevent slippage.

2. The implant of claim 1, wherein said retaining member made of surgical metal.

3. The implant of claim 1 wherein said posterior wing is downwardly disposed at an angle between 75 degrees and 80 degrees from the longitudinal portion.

4. The implant of claim 1 wherein said superior wing is upwardly disposed at an angle between 75 degrees and 80 degrees at the other end of the longitudinal portion.

5. A method of stabilizing a fractured or luxated cervical vertebra comprising the steps of:
    exposing the pre-vertebral space;
    widely resecting the intervertebral disk in the intervertebral space; and
    coupling the anterior portion of the body of the fractured and luxated vertebra to the posterior portion of the body of an adjacent lower vertebra.

* * * * *